US010137185B2

(12) United States Patent
Stephanie et al.

(10) Patent No.: US 10,137,185 B2
(45) Date of Patent: Nov. 27, 2018

(54) PAP PEPTIDE ANALOGUES

(71) Applicant: THE NOTTINGHAM TRENT UNIVERSITY, Nottingham (GB)

(72) Inventors: McArdle Stephanie, Nottingham (GB); Rees Robert, Nottingham (GB); A. Graham Pockley, Nottingham (GB); Jaimy Saif, Nottingham (GB)

(73) Assignee: Nottingham Trent University, Nottinghamshire (GB)

( * ) Notice: Subject to any disclaimer, the term of this patent is extended or adjusted under 35 U.S.C. 154(b) by 0 days.

(21) Appl. No.: 15/302,954

(22) PCT Filed: Apr. 9, 2015

(86) PCT No.: PCT/GB2015/051084
§ 371 (c)(1),
(2) Date: Oct. 7, 2016

(87) PCT Pub. No.: WO2015/155537
PCT Pub. Date: Oct. 15, 2015

(65) Prior Publication Data

US 2017/0106064 A1 Apr. 20, 2017

(30) Foreign Application Priority Data

Apr. 11, 2014 (GB) .................................. 1406581.7

(51) Int. Cl.
*A61K 38/00* (2006.01)
*A61K 39/00* (2006.01)
*C12N 9/16* (2006.01)

(52) U.S. Cl.
CPC ............ *A61K 39/0011* (2013.01); *C12N 9/16* (2013.01); *C12Y 301/03002* (2013.01); *C12Y 301/03005* (2013.01); *A61K 2039/53* (2013.01); *A61K 2039/57* (2013.01)

(58) Field of Classification Search
None
See application file for complete search history.

(56) References Cited

U.S. PATENT DOCUMENTS

2004/0142890 A1 7/2004 McNeel

FOREIGN PATENT DOCUMENTS

| | | |
|---|---|---|
| WO | 2005090560 | 9/2005 |
| WO | 2015155537 | 10/2015 |

OTHER PUBLICATIONS

Engelhard, Current Opinion in Immunology vol. 6 p. 13 (1994) (Year: 1994).*
Guo, et al Nature vol. 360 p. 384 (1992) (Year: 1992).*
Rammensee et al, Immunogenetics vol. 41 p. 178 (1995) (Year: 1995).*
Shastri et al J. Immunol. 1995 vol. 155 p. 4339 (Year: 1995).*
Bode, et al. "CpG DNA as a vaccine adjuvant", Expert Review of Vaccines (2011) 10(4): 499-511.
Boyle, et al. "Cancer incidence and mortality in Europe" Annals of Oncology, (2004) 16(3): 481-8.
Christensen et al. "Melan-A/MART1 analog pep-tide triggers anti-myeloma T cells through crossreactivity with HM1.24" J. Immunotherapy (2009) 32: 613-621.
Cole, et al. "The genetics of cancer-a 3D model" Nat. Genet. (1999) 21: 38-41.
Cunha, et al. "Tissue-specificity of prostate specific antigens: comparative analysis of transcript levels in prostate and non-prostatic tissues", Cancer Letters (2006) 236(2): 229-38.
Durrant, et al. "Using monoclonal antibodies to stimulate antitumor cellular immunity" Expert Review of Vaccines (2011) 10(7): 1088.
Fourcade, et al. "Immunization with analog peptide in combination with CpG and montanide expands tumor antigen-specific CD8+ T cells in melanoma patients" J. Immunother (2008) 31: 781-791.
Geary, et al. "Prostate cancer vaccines", Oncoimmunology (2013) 2(5): 24523.
Gupta, et al. "Sipuleucel-T for therapy of asymptomatic or minimally symptomatic, castrate-refractory prostate cancer: an update and perspective among other treatments", OncoTargets and Therapy (2011) 4:79-96.
Harada, et al. "Prostate-related antigen-derived new peptides having the capacity of inducing prostate cancer-reactive CTLs in HLA-A2 prostate cancer patients", Oncology Reports (2004) 12: 601-607.
Hardwick, et al. "An analogue peptide form the Cancer/Testis antigen PASD1 induces CD8+ T cell responses against naturally processed peptide" Cancer Immunity (2013) 1:16.
Higano, et al. "Integrated data from 2 randomized, double-blind, placebo-controlled, phase 3 trials of active cellular immunotherapy with sipuleucel-T in advanced prostate cancer", Cancer (2009) 115: 3670-3679.
Johnson, et al. "Safety and immunological efficacy of a prostate cancer plasmid DNA vaccine encoding prostatic acid phosphatase (PAP)", Vaccine (2006) 24: 293-303.
Li, et al. "Design of a potent CD1d-binding NKT cell ligand as a vaccine adjuvant" Proc Natl. Acad. Scie. U S A 2010 107(29): 13010-5.
McNeel et al. "Safety and Immunological Efficacy of a DNA Vaccine Encoding Prostatic Acid Phosphatase in Patients with Stage Do Prostate Cancer", J. Clin. Oncol. (2009) 27(25): 4047-4054.
Mistry, et al. "Meta-Analysis of Prostate-Specific Antigen and Digital Rectal Examination as Screening Tests for Prostate Cancer" J. Am. Board Fam. Pract. (2003) 16(2): 95-101.

(Continued)

*Primary Examiner* — Sheela J. Huff
(74) *Attorney, Agent, or Firm* — Workman Nydegger

(57) ABSTRACT

The application provides a polypeptide comprising the sequence SLMTNLAAL (SEQ ID NO: 8), Ser 13 to Leu 21 of amino acid sequence shown in FIG. 1 or SEQ ID No 1, and having HLA-A2 haplotype binding activity, or a polynucleotide encoding said polypeptide. Vaccines containing the polypeptide or polynucleotides encoding the polypeptide are also provided.

22 Claims, 12 Drawing Sheets

Specification includes a Sequence Listing.

(56) References Cited

OTHER PUBLICATIONS

Nemunaitis "Vaccines in cancer: GVAX, a GM-CSF gene vaccine" Expert Review of Vaccines (2005) 4(3) 259-74.
O'Keefe, et al. "Comparative analysis of prostate-specific membrane antigen (PSMA) versus a prostate-specific membrane antigen-like gene", Prostate (2004) 58(2):200-10.
Olson, et al. "HLA-A2-restricted T-cell epitopes specific for prostatic acid phosphatase" Cancer Imunol. Immunother (2010) 59: 943-953.
Pudney, et al. "DNA vaccination with T-cell epitopes encoded within Ab molecules induces high-avidity anti-tumor CD8+ T cells", Eur. J. Immunol, (2010) 40: 899-910.
Saif, et al. "Novel prostate acid phosphatase-based peptide vaccination strategy induces antigen-specific T-cell responses and limits tumour growth in mice", Eur. J. Immunol. (2014) 44:994-1004.
Siegel, et al. "Cancer Statistics" CA Cancer J. Clin. (2013) 63:11-30.
Snyder, et al. "Perspectives on immunotherapy in prostate cancer and solid tumors: where is the future?" Seminars in Oncology (2013) 40(3): 347-60.
Speetjens, et al. "Induction of p53-specific immunity by a p53 synthetic long peptide vaccine in patients treated for metastatic colorectal cancer" Clinical Cancer Research (2009) 15(3): 1086-95.
Valmori, et al. "Enhanced Generation of Specific Tumor-Reactive CTL in Vitro by Selected Melan-A/MART-1 Immunodominant Peptide Analogues", Journal of Immunology (1998) 160: 1750-1758.
Zhang, et al. "Vaccination with a DNA vaccine based on human PSCA and HSP70 adjuvant enhances the antigen-specific CD8+ T-cell response and inhibits the PSCA+ tumors growth in mice", J. Gene Medicine (2007) 9(8): 715-26.
International Search Report and Written Opinion for PCT/GB2015/051084 dated Jul. 16, 2015.

* cited by examiner

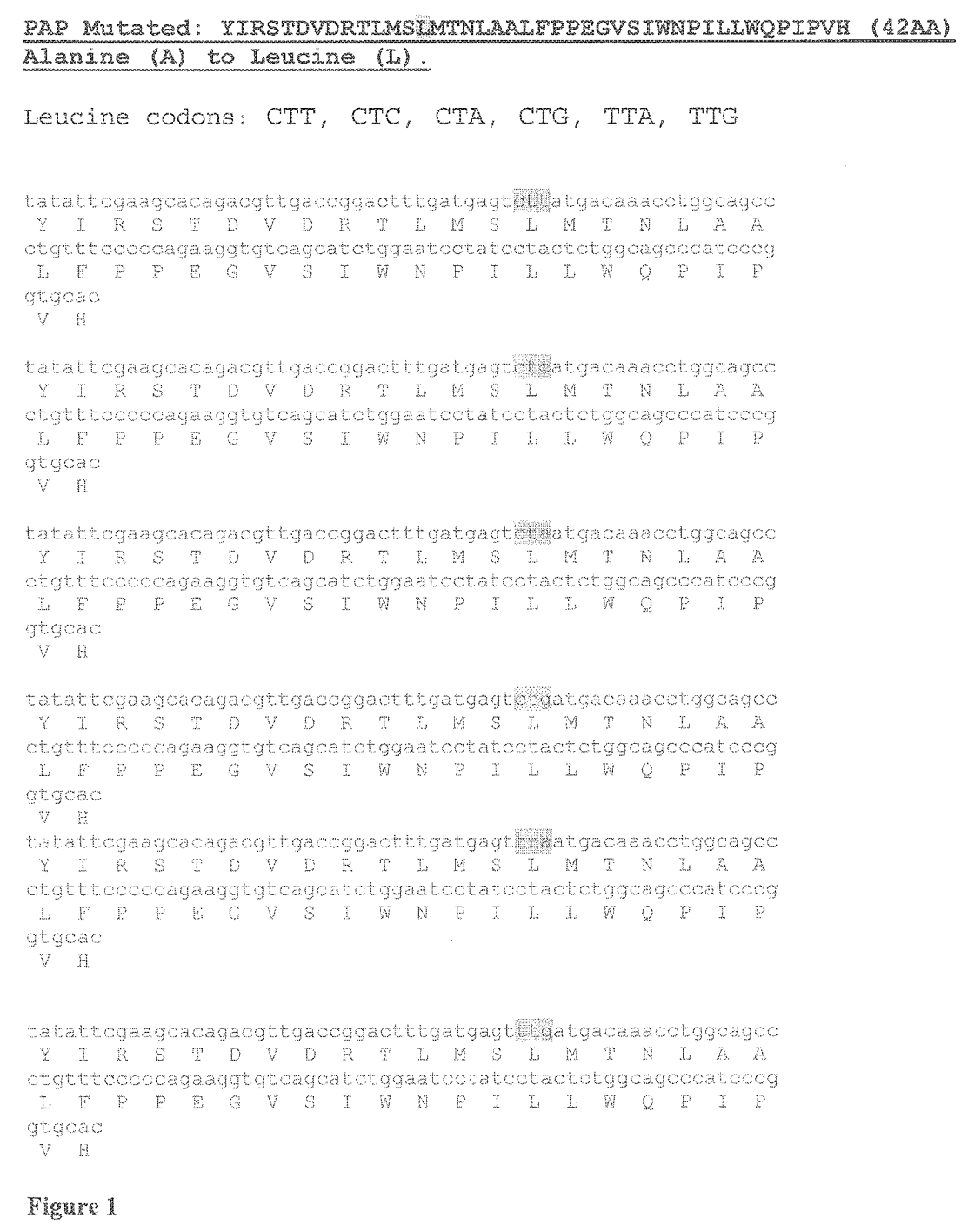

PAP Mutated: YIRSTDVDRTLMSLMTNLAALFPPEGVSIWNPILLWQPIPVH (42AA)
Alanine (A) to Leucine (L).

Leucine codons: CTT, CTC, CTA, CTG, TTA, TTG

```
tatattcgaagcacagacgttgaccggactttgatgagtcttatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H

tatattcgaagcacagacgttgaccggactttgatgagtctcatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H

tatattcgaagcacagacgttgaccggactttgatgagtctaatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H

tatattcgaagcacagacgttgaccggactttgatgagtctgatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H
tatattcgaagcacagacgttgaccggactttgatgagtttaatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H

tatattcgaagcacagacgttgaccggactttgatgagtttgatgacaaacctggcagcc
 Y  I  R  S  T  D  V  D  R  T  L  M  S  L  M  T  N  L  A  A
ctgtttcccccagaaggtgtcagcatctggaatcctatcctactctggcagcccatcccg
 L  F  P  P  E  G  V  S  I  W  N  P  I  L  L  W  Q  P  I  P
gtgcac
 V  H
```

Figure 1

PAP PEPTIDE ANALOGUES

CROSS REFERENCE TO RELATED APPLICATIONS

This application claims benefit of priority under 35 U.S.C. § 371 of International Application PCT/GB2015/051084, filed on 9 Apr. 2015, which claims the benefit of and priority to British Patent Application GB 1406581.7, filed on 11 Apr. 2014. The contents of the foregoing listed International Application and the British application are hereby incorporated by reference in their entirety, including the various attachments filed therewith.

BACKGROUND

The invention relates to peptide analogues from prostate acidic phosphatase (PAP) and their use as vaccines. In particular, the analogue includes the change of alanine to leucine at position 115 of PAP which has been found to be particular advantageous.

Prostate cancer is the most common form of male cancer in developed countries and cases are rising among men under 50. Every year, more than 32,000 British men are diagnosed and 10,000 die from the disease [1,2]. At present there is no standard treatment available for patients with biochemical recurrence in the absence of radiographically-visible metastases [3]. A long-held dream of tumour immunologists is to harness the specificity and sensitivity of the immune response and induce specific protective anti-tumour immunity. Unfortunately, for most cancers, the specific antigenic determinants on which vaccination strategies can be based are weakly immunogenic self-antigens which are comparatively poor at inducing robust, protective anti-tumour responses. Developing cancer vaccines that can overcome immune evasion and the tolerogenic capacity of self-antigens and induce protective immune responses is therefore essential for the development of new immunotherapies for aggressive disease.

Several tumour-associated antigens have been reported to be expressed by prostate cancer cells. These include prostate-specific membrane antigen (PSMA), prostate-specific antigen (PSA), and prostate acidic phosphatase (PAP) [4]. The prostate-restricted expression and overexpression of PAP in prostate cancer makes this antigen an ideal candidate on which to base a cancer vaccine [5]. The potential of the PAP antigen has recently been illustrated in the form of an FDA-approved vaccine for advanced prostate cancer which has been demonstrated to increase the overall survival of patients. The vaccine consists of in vitro patient-derived mononuclear cells transfected with the entire prostatic acid phosphatase (PAP)-protein fused to GM-CSF (Provenge, sipuleucel-T) [6]. However, the production of an entire protein vaccine is time-consuming and costly, and the exact region of the PAP protein which is responsible for eliciting the therapeutic effect remains unknown. Furthermore, in other settings, vaccination using long peptides rather than whole protein has been shown to provide a more efficient and robust protective immune response [7]. An important feature of PAP in the context of a vaccine for prostate cancer is that sequences contained within the PAP molecule exhibit a high degree of homology between the murine and human proteins.

This means that pre-clinical (murine) models focussed on inducing protective anti-tumour immunity using a PAP-based vaccine present similar challenges relating to the presence of tolerance to 'self' antigens such as PAP to those that are encountered in the clinical setting. Results obtained using such a mouse model therefore have a better potential for being successfully translated into patients.

WO 2005/090560 relates to peptides from PAP as positions 135 and 161 which were identified as candidate peptides for vaccine-based immunotherapy. The PAP 135 sequence ILLWQPIPV (amino acids 33-41 of SEQ ID NO: 1) showed a strong binding to HLA-A2.

The current invention focuses on a mutation at position 115 of PAP from Ala to Leu. This has been unexpectedly found to produce enhanced immune response. This suggests that PAP peptides encoding the analogue, or DNA vaccines encoding the analogue will produce an improved immune response compared to sequences with the native PAP 115 sequence. The analogue has also been found to work as both small and large peptides, allowing the production of peptides with multiple epitopes.

This was unexpected. Changing the amino acid at position 115 to, for example isoleucine, valine or methionine did not enhance the HLA binding score and immune response.

The invention provides a polypeptide comprising the sequence SLMTNLAAL (SEQ ID NO: 8) having HLAA2 haplotype binding activity or a polynucleotide encoding said polypeptide.

That is, this is the polypeptide comprising the sequence from Ser 13 to Leu 21 of the amino acid sequence shown in FIG. 1 or SEQ ID No: 1.

Polypeptides may comprise at least 9, 15, 20, 25, 30, 35, 45 or 55 or less than 60 amino acids of the native PAP amino acid sequence, provided that the sequence contains the polypeptide sequence corresponding to Ser 13 to Leu 21.

Polypeptides or polynucleotides comprising the sequence Met 12 to Gly 26 of the amino acid sequence shown in FIG. 1 or SEQ ID No: 1 are also provided. That is, they comprise the sequence MSLMTNLAALFPPEG (SEQ ID NO: 9). These are being found to have a Syfpeithi score of 33, and have HLA-DR1 haplotype binding activity, as well as HLA-A2 activity.

The Syfpeithi database is a database of more than 7000 peptide sequences known to bind class I and class II MHC molecules compiled from published records. This allows potential motifs and their ability to bind HLA haplotypes to be identified with a high degree of accuracy. The HLA haplotype binding activity may be determined using that database (www-dot-syfpeithi-dot-de).

A further embodiment of the invention provides a polypeptide or polynucleotide comprising the sequence Asp 8 to Phe 22 of the amino acid sequence shown in FIG. 1 or SEQ ID No: 1. That is, it comprises the sequence DRTLMSLMTNLAALF (SEQ ID NO: 10). This is a 15 Mer. The mutation to use leucine has been found to increase the Syfpeithi score from 22 to 30. It has the following haplotype activity, HLA-DR4 and HLA-A2 activity.

A still further aspect of the invention provides a polypeptide comprising the sequence Ser 13 to His 42 of the amino acids shown in FIG. 1 or SEQ ID No: 1.

The sequence includes not only the 9 Mer sequence SLMTNLAAL (SEQ ID NO: 8) but additionally comprises the sequence ILLWQPIPV (amino acids 33-41 of SEQ ID NO: 1) which has HLA-A2 activity.

A still further aspect of the invention provides a polypeptide or polynucleotide according to the invention comprising the sequence Arg 9 to Pro 23 of the amino acid sequence shown in FIG. 1 or SEQ ID No: 1. That is, RTLMSLMTNLAALFP (SEQ ID No: 14). This has been found to increase the Syfpeithi score from 22 to 23 with the leucine mutation. It has the following HLA-haplotype: HLA-DR1 and HLA-A2 activity.

A still further aspect of the invention provides the sequence Tyr 1 to His 42 of the amino acid sequence shown in FIG. 1 or SEQ ID No: 1. The advantage of this sequence is that is contains a number of different haplotype sequences.

FIG. 1 shows the same polypeptide sequence, but with different leucine codons at amino acid position 14. That is, the leucine codon may be selected from CTT, CTC, CTA, CTG, TTA or TTG. Typically the leucine codon is CTT.

That is, the native sequence for PAP is mutated at position 115 so that instead of the sequence encoding alanine, it then encodes leucine.

The polypeptide may be incorporated into a polypeptide sequence encoding at least a part of an antibody or immunoglobulin, for example through the use of the commercially available technology known as "Immunobody™" described below. The polypeptide may also be fused, for example, to a part of a gene sequence from granulocyte-macrophage colony stimulating factor (GM-CSF), such as that provided by the GVAX technology described below.

The polypeptide may also be fused to a sequence, or used in conjunction with an adjuvant, comprising a sequence from HSP-70, Shiga toxin, alpha-GAL-Ser, or TLR agonists such as CpG or PolyIC.

HSP-70 has been known to be used as an adjuvant in combination with DNA vaccines. This heat shock protein induces antigen-specific cellular and humoral immunity (see for example Zang X et al, J Gene Med. 2007 9(8) 715-26).

Microbial proteins in the cytosol of host cells activate $CD8^+$ cytotoxic T lymphocytes (CTLs). Once activated, CTLs lyse infected cells and secrete cytokines that stimulate other immune cells at the site of infection. Because of this modified bacterial toxins have been used to deliver vaccine antigens. Accordingly, the polypeptides of the invention may be fused to or be used in combination with a bacterial toxin such as Shiga toxin, anthrax toxin or diphtheria toxin.

Synthetic oligodeoxynucleotides containing unmethylated CpG motifs, have been found to trigger cells that express TOLL-like receptor 9, to mount immune responses characterised by the production of Th1 and proinflammatory cytokines. When used as vaccine adjuvants CpG improves the function of professional antigen-presenting cells and boosts the generation of humoral anti-cellular vaccine-specific immune responses. See for example, Bode C et al, Expert Rev Vaccines 2011 10(4) 499-511.

PolyIC is a synthetic double-stranded RNA made of polyinosine-polycytidylic acid that can activate the immune response. It is commercially available from, for example, InvivoGen, under the trademark VacciGrade, and acts as a vaccine adjuvant.

Alpha-GAL-Ser (Alpha-Galactosylceramide) is a glyco lipid composed of alpha-linked sugar and lipid moieties. It has been described for use as a vaccine adjuvant (see, for example, Li X, Fujio M, Imamura M, Wu D, Vasan S, Wong C H, Ho D D, Tsuji M. Proc Natl Acad Sci USA. 2010 Jul. 20; 107(29):13010-5. doi: 10.1073/pnas.1006662107

Polypeptides may be fused to a ubiquitin or secretory leader sequence. This allows a polypeptide produced by a polynucleotide encoding the protein to be secreted from the cell.

pVAX1 or GVAX vectors comprise a polynucleotide of the invention.

pVAX1™ is a 3.0 kb plasmid vector designed for use in the development of DNA vaccines. It is supplied by Invitrogen a part of Life Technologies Corporation and is supplied as catalog number V160-20 (as of 2 Mar. 2012). The sequence of pVAX1 is shown in the sequence listing SEQ ID No: 12. A schematic diagram of pVAX1 is shown in FIG. 2. The vector is also available and may be used with a lacZ gene, containing β-galactosidase as a control vector. The kanamycin resistance gene of pVAX1 may be replaced by a non-antibiotic based marker.

GVAX is a granulocyte-macrophage colony stimulating factor (GM-CSF) gene transfected tumour cell vaccine which has been demonstrated to produce good vaccine activity with other PAP peptides, as have other DNA or polynucleotide vaccines (Nemunaitis J., Expert Rev. Vaccines 2005 4(3) 259-74), McNeel D G et al J. Clin. Oncol. 2009, 27(25) 4047-4054, Geary S M et al. Oncoimmunology 2013, 2(5) 24523).

An alternative DNA vaccine may utilise Immunobody™ DNA vaccine technology. Immunobody™ is a human antibody or fusion protein which is engineered to express helper cell and CTL epitopes from tumour antigens that are overexpressed by cancer cells. The Immunobody™ technology is commercially available from Scancell Ltd, Nottingham U.K. See, for example, Pudney et al Eur. J. Immunol. 2010, 40:899-910 and Durrant L G et al Expert. Rev, Vaccines 2011 10(7) 1088. The technology inserts tumour associated epitopes into the structure of antibodies. Antibodies have been found to be good DNA vectors for stimulating immune responses. Responses are 100-1000 fold more effective than protein, peptide or antigen DNA immunisation.

Polynucleotides encoding the peptide, alone or fused to a polynucleotide vaccine as described above, may be administered, for example, intravenously or intramuscularly. Immunobody™-based vaccines have been previously found to persist at intramuscular injection sites for 90 days and lymph nodes for 7 days and induce strong $CD8^+$ responses (Durrant et al Supra).

The polynucleotide sequence encoding the peptides of the invention may also be modified by attaching to the sequence encoding the peptide, a ubiquitin sequence and/or a leader sequence for allowing the secretion of the peptide, prior to incorporation into a vector such as those described above.

Vaccines comprising the polynucleotides or polypeptides of the invention are also provided. Polypeptides or polynucleotides of the invention may be used as part of a vaccine against prostate cancer.

Methods of preventing or treating prostate cancer comprise administering a polypeptide or polynucleotide of the invention are also provided.

BRIEF DESCRIPTION OF THE DRAWINGS

The invention will now be described by way of example only with reference to the following Figures:

FIG. 1 shows a 42 amino acid sequence from PAP in which alanine has been replaced by leucine at position 14 (position 115 of the native PAP protein), corresponding to SEQ ID NO. 1. The Figure shows six alternative polynucleotide sequences encoding the mutated peptide in which alternative codons coding for leucine have been inserted into the polynucleotide, with the codon encoding alanine (gct) replaced by the leucine codon, corresponding to SEQ ID NOS. 2-7, respectively.

DETAILED DESCRIPTION

PAP-115-123 Specific IFNγ Responses Generated by PBMCs from Patients with Prostate Cancer To determine the presence of circulating T cells specific for PAP-115-123 in humans, PBMCs from HLA-A2 positive patients with prostate cancer and individuals with benign disease were used. Cryopreserved PBMCs were thawed, washed and restimulated for 7 days with PAP-114-129 epitope peptide. The cells were then washed and rested overnight, at which time $4\times10^4$ cells were added to each well of an ELISPOT plate. PAP-115-123 epitope peptide (1 μg) was added to each well and the cells cultured for 48 hours. The plates were developed according to the manufacturer's instructions. PBMCs cultured with no peptide were used as controls. A PAP-115-123 specific IFNγ response was seen in 7 of the 10 PBMC samples from patients with prostate cancer (FIG. 3), and this was significantly greater than that observed in controls (splenocytes pulsed with no peptide, $p<0.05$, unpaired t-test). The number of IFNγ spots generated by PBMCs from one of the patients was as high as 220 (vs 60 spots for the control). The number of spots generated by PBMCs for the other 6 patients with prostate cancer ranged between 50 and 100 (vs 10-20 in controls). Although some of the PBMCs from individuals with benign disease generated 50-100 spots, the number of spots in the control wells was also high. As a consequence, no PAP-115-123 specific IFNγ response was seen in any of the samples that had been obtained from individuals with benign disease.

Figure 4:
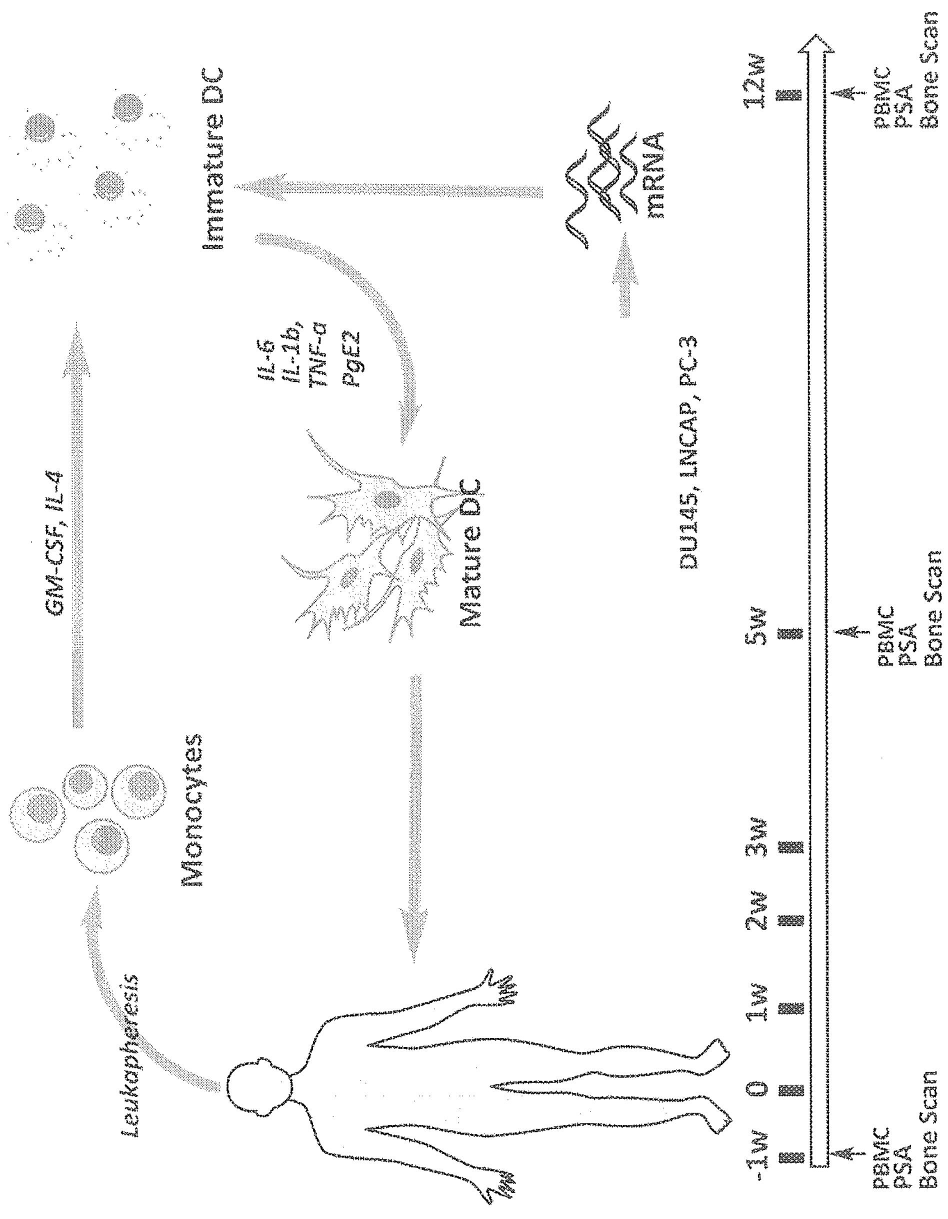
FIG. 4. The flow chart of Norway clinical trial. Monocytes were isolated from patients with prostate cancer and cultured in vitro. mRNA isolated from the prostate cancer cell lines DU145, LNCAP and PC3 were transfected into immature dendritic cells (DCs). The DCs were then allowed to mature and were re-infused back into the patient. PBMCs isolated a week before (pre-vaccination) and 12 weeks after immunisations (post-vaccination) were used in this study. The patients were categorised as responders and non-responders based on the PSA levels and also metastatic state of the disease based on bone scans post immunisation.

PAP-115-123 Specific IFNγ Responses Generated by PBMCs from Patients with Prostate Cancer Following Treatment with DCs that had been Transfected with mRNA Isolated from the Prostate Cancer Cell Lines (DU145, LNCaP and PC3) as part of the Norwegian Clinical Trial The presence of circulating PAP-115-123 specific T cells in PBMCs isolated from patients with prostate cancer following treatment with DCs that had been transfected with mRNA isolated from the prostate cancer cell lines (DU145, LNCaP and PC3) as part of a Norwegian Clinical Trial which was performed by Professor Gustav Gaudernack was determined on the basis of their responsiveness to PAP-derived peptides. In the trial, DCs were isolated from patients with prostate cancer and cultured DCs were transfected with mRNA isolated from the prostate cancer cell lines (DU145, LNCaP and PC3). The matured DCs were re-infused back into the patients (FIG. 4). PBMCs samples isolated a week before the immunisation (pre-vaccination) and 12 weeks after the immunisation (post-vaccination) were used in this study.

Figure 5:
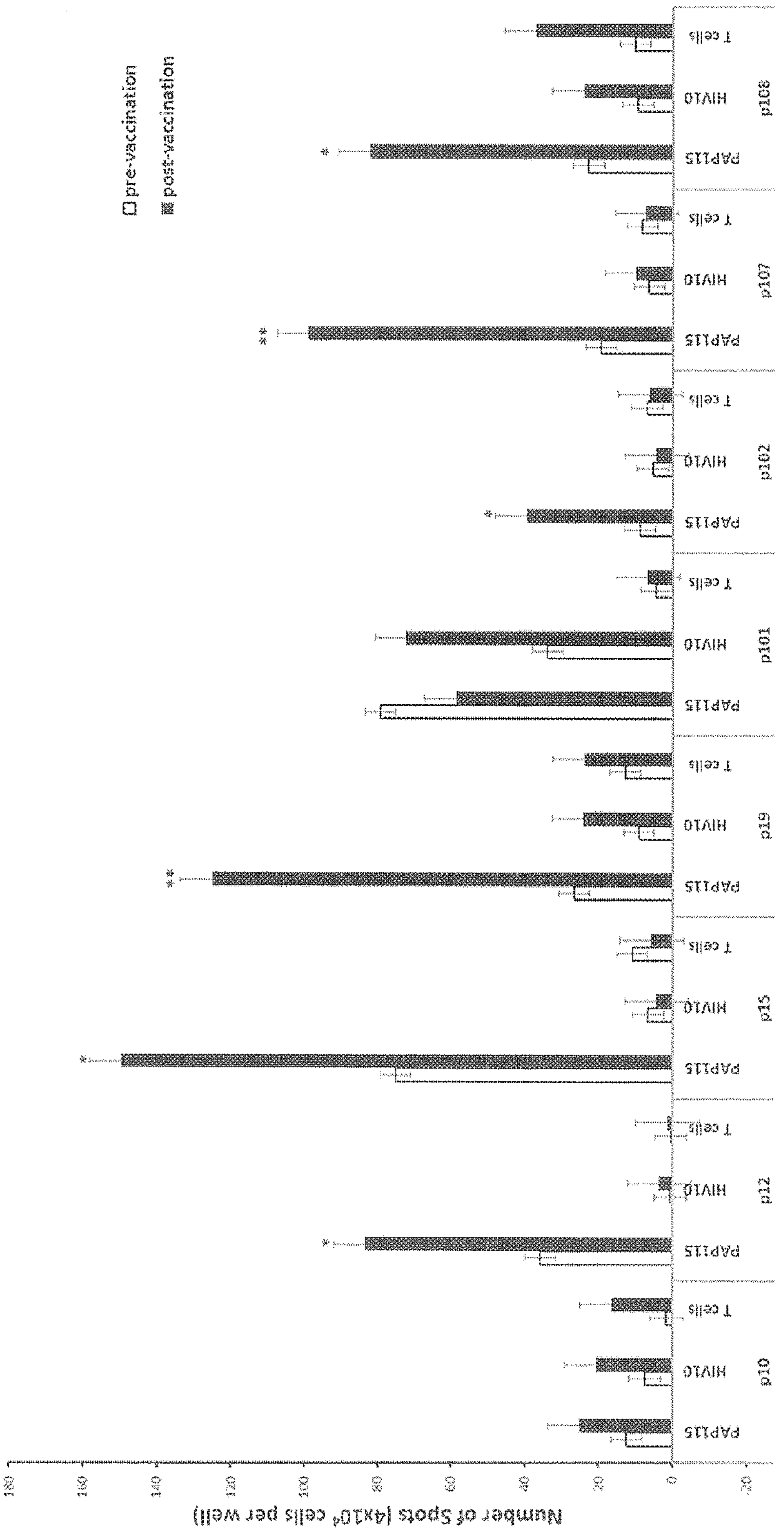
FIG. 5. IFNγ response of PBMCs isolated from patients with prostate cancer who had responded to the therapy and were categorised as being 'responders' on the basis of the criteria detailed above (Norway Clinical Trial) after re-stimulation with PAP-115-123 epitope peptide (10 μg), as determined using the ELISPOT assay. PBMCs isolated pre-vaccination (black bars) and post vaccination (red bars) are compared. Patient samples are represented as p10, p12, p15 etc. The cryopreserved PBMCs were washed and rested overnight, at which time $4\times10^4$ cells were added to each well of an ELISPOT plate. PAP-115-123 epitope peptide (10 μg) was added to each well and the cells cultured for 48 hours. The plates were then washed according to the manufacturer's protocol. PBMCs cultured with an HIV-derived peptide or no added peptide were used as controls. Comparisons of means (±SEM) between groups (pre-vaccination or post-vaccination PBMCs) are made using an unpaired t test.

The patients were categorised as being 'responders' and 'non-responders' on the basis of PSA levels and also on the extent of metastasis, as identified using bone scans. PAP-115-123 specific IFNγ responses in 8 pre-vaccination PBMC samples and 8 post-vaccination PBMC samples were assessed. For the assay, cryopreserved PBMCs were thawed, washed and rested overnight, at which time $4\times10^4$ cells were added to each well of an ELISPOT plate. PAP-115-123 epitope peptide (10 μg) was added to each well and cells were cultured for 48 hours. The plates were developed according to the manufacturer's protocol. PBMCs cultured with HIV-derived peptide or no peptide were used as the control. Out of the 8 samples tested, 6 samples from patients post-vaccination exhibited a significantly higher PAP-115-123 specific IFNγ response, as compared to the respective pre-vaccination samples ($p<0.05$, unpaired t-test) (FIG. 5). The patients that showed significantly higher PAP-115-123 specific IFNγ post vaccination were p12, p15, p19, p102, p107 and p108. The number of spots generated by the post-vaccination samples of these patients ranged from 60-160 spots (vs 10-30 spots in the pre-vaccination samples).

Figure 6:
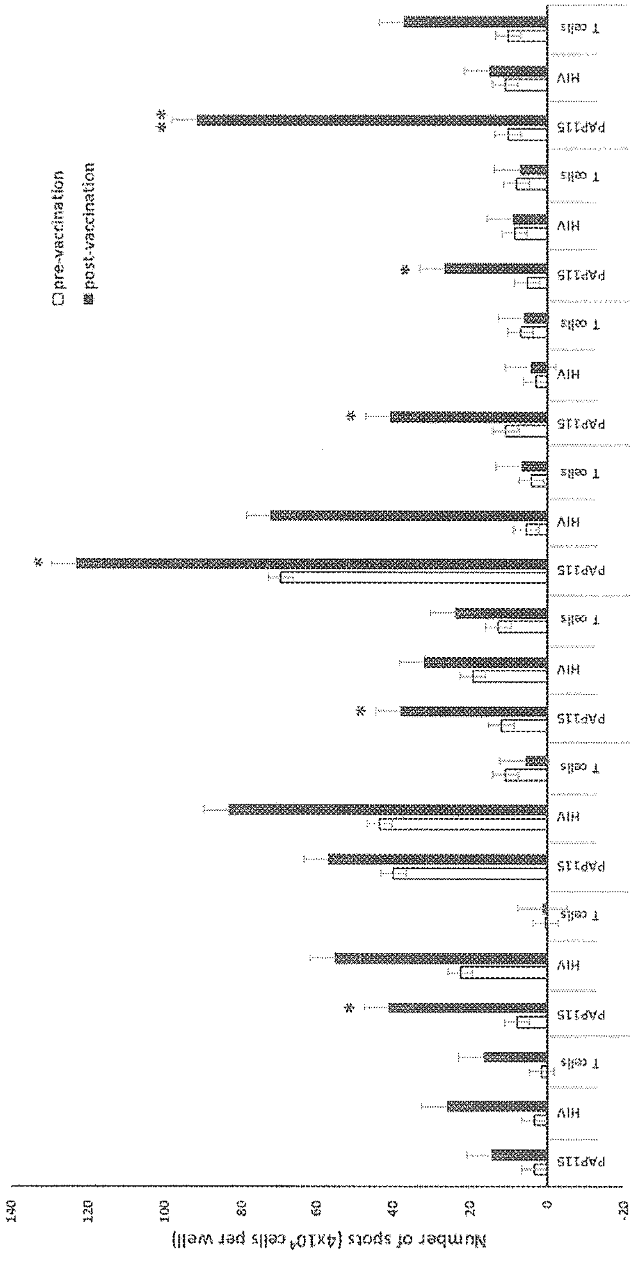
FIG. 6. IFNγ response of PBMCs isolated from patients with prostate cancer who had responded to the therapy and were categorised as being 'responders' on the basis of the criteria detailed above after re-stimulation with PAP-115-123 epitope peptide (1 μg), as determined using the ELISPOT assay. PBMCs isolated pre-vaccination (black bars) and post-vaccination (red bars) are compared here. Patient samples are represented as p10, p12, p15 etc. The cryopreserved PBMCs were washed and rested overnight, at which time $4\times10^4$ cells were added to each well of an ELISPOT plate. PAP-115-123 epitope peptide (1 μg) was added to each well and the cells cultured for 48 hours. The plates were then washed according to manufacturer's protocol. PBMCs cultured with HIV-derived peptide or no added peptide were used as controls. Comparisons of means (±SEM) between groups (pre-vaccination or post-vaccination PBMCs) are made using an unpaired t test.

To assess if the PAP-115-123 specific T cells in these PBMC samples could be stimulated by a lower concentration of peptide, PBMCs were cultured with 1 μg of PAP-115-123 epitope for 48 hours. PBMCs cultured with HIV-derived peptide or no peptide were used as controls. Out of the 8 samples tested, 6 samples from patients post-vaccination showed a significantly higher PAP-115-123 specific IFNγ response compared to their respective pre-vaccination samples ($p<0.05$, unpaired t-test) (FIG. 6). The patients that exhibited significantly higher PAP-115-123 specific IFNγ responses post-vaccination were p12, p19, p101, p102, p107 and p108. The number of spots obtained using samples from patients post-vaccination ranged from 60-140 spots (vs 10-30 spots in the pre-vaccination samples). Patient p15 who showed a significant response with 10 μg of PAP-115-123, did not show a similar response when his PBMCs were stimulated with 1 μg of PAP-115-123. In contrast, PBMCs from patient p101 generated a marked IFNγ response when restimulated with 1 μg of PAP-115-123, but failed to respond when re-stimulated with 10 μg of PAP-115-123. The number of background spots was slightly higher when PBMCs were re-stimulated with 1 μg of PAP-115-123.

PAP-115-123 Specific IFNγ Responses Generated by PBMCs from Patients with Prostate Cancer Following Treatment with DCs that had Responded to Treatment.

In vitro stimulation of PBMCs: A 10-day ELISPOT assay was performed to determine the precursor frequencies of peptide specific T cells. On day 1 PBMCs were plated (2×106 cells/ml) into 24 well plates in quadruplicates in 2 ml of RPMI-1640 medium containing L-glutamine, penicillin, streptomycin and 10% AB serum (T-cell medium). The cells were incubated at 37° C., 5% CO2. On day 2, the media was replenished with IL-2 (20 U/ml) and IL-7 (5 ng/ml). On day 3, 10 μg/ml peptide antigen or Flu antigen was added to respective wells. On day 7, 500 ul of supernatants were collected for ELISA. The cells were then washed and replenished with fresh IL2 (20 U/ml). IFNγ elispot assay was performed on day 8 were performed according to manufacturer's protocol (R&D systems).

Figure 7:
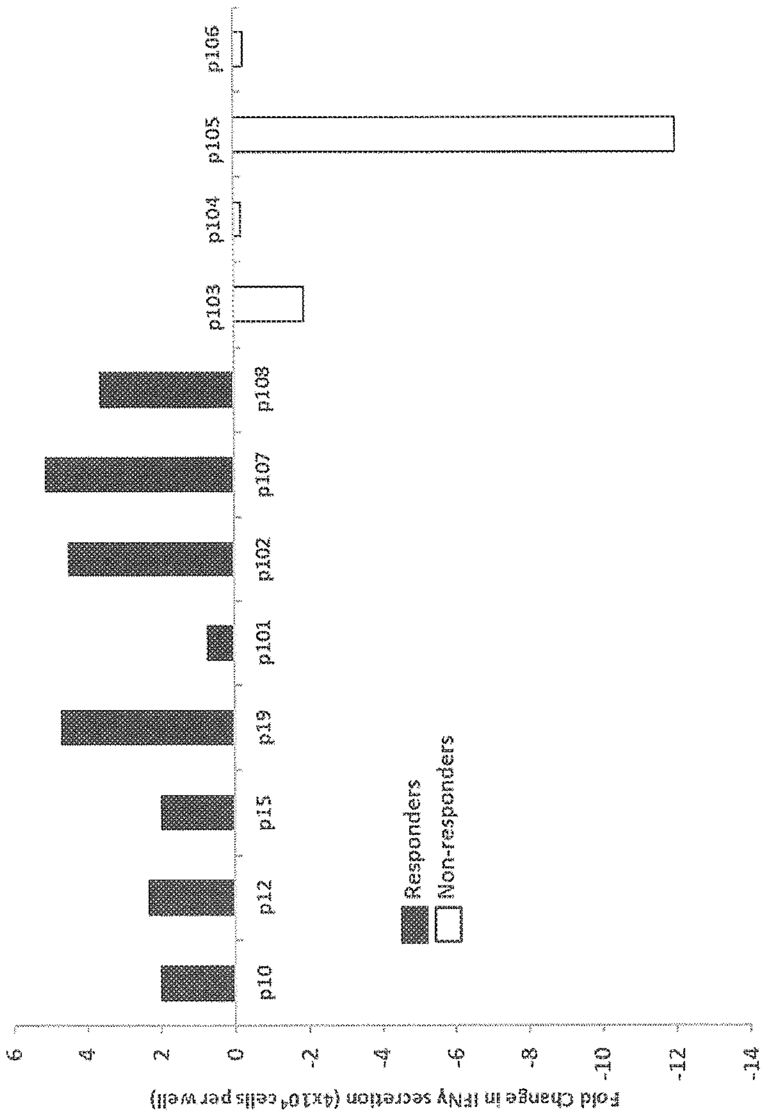
FIG. 7. Fold change in the IFNγ response generated by PBMCs isolated from patients with prostate cancer from the Norway Clinical Trial after restimulation with PAP-115-123 epitope peptide (10 μg), as determined using the ELISPOT assay. Patients that were reported to have responded to the treatment (p10, p12, p15, p19, p101, p102, p107, p108) are indicated by red bars. The patients that were reported to have failed to respond to the treatment (p103, p104, p105, p109) are indicated by white bars. The cryopreserved PBMCs were washed and rested overnight, at which time $4\times10^4$ cells were added to each well of an ELISPOT plate. PAP-115-123 epitope peptide (10 μg) was added to each well and the plates cultured for 48 hours. The plates were then washed according to the manufacturer's protocol. PBMCs cultured with HIV-derived peptide or no added peptide were used as control.
Figure 8:
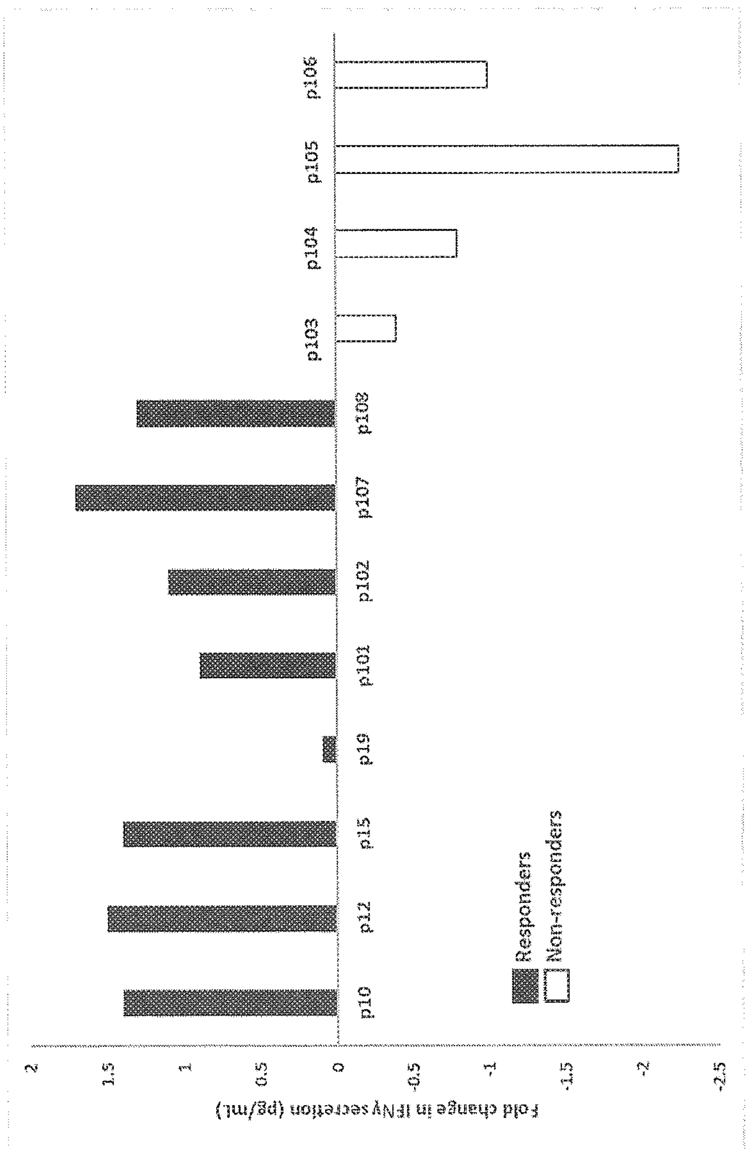
FIG. 8. Fold change in the IFNγ response generated by PBMCs isolated from patients with prostate cancer from the Norway Clinical Trial after re-stimulation with of PAP-115-123 epitope peptide (10 μg), as assessed using an ELISA. Patients that were reported to have responded to the treatment (p10, p12, p15, p19, p101, p102, p107, p108) are indicated by red bars. Patients that were reported to have failed to respond to the treatment (p103, p104, p105, p109) are indicated by white bars. The cryopreserved PBMCs were washed and rested overnight, at which time $4\times10^4$ cells were added to each well of a 96 well plate. PAP-115-123 epitope peptide (10 μg) was added to each well and the plates cultured for 48 hours. Supernatants were harvested and analysed for IFNγ secretion.

PAP-115-123 specific IFNγ responses generated by PBMCs from 8 patients with prostate cancer that positively responded to the vaccination module (responders) in the Norway Clinical Trial and 4 patients that failed to show a clinical response (non-responders) were assessed. Cryopreserved PBMCs were thawed, washed and rested overnight, at which time $4\times10^4$ cells were added to each well of an ELISPOT plate. PAP-115-123 epitope peptide (10 μg) was to each well and cells were cultured for 48 hours. The plates were developed according to the manufacturer's protocol. PBMCs cultured with HIV-derived peptide or no peptide were used as controls. A 2-4 fold higher PAP-115-123 specific IFNγ response was observed using PBMCs from 8 of the responder patients and 2-12 fold decreases in the IFNγ response was observed using PBMCs from 4 of the non-responder patients (FIG. 7). IFNγ secretion in these samples was confirmed by analysing harvested supernatants using an R&D Systems ELISA (FIG. 8). The ELISA identified a 1-1.5 fold higher IFNγ levels in all responders (except in p19) and a 2-2.5 fold lower levels in non-responders, when the pre-vaccination sample was compared to the post vaccination samples.

Figure 9:
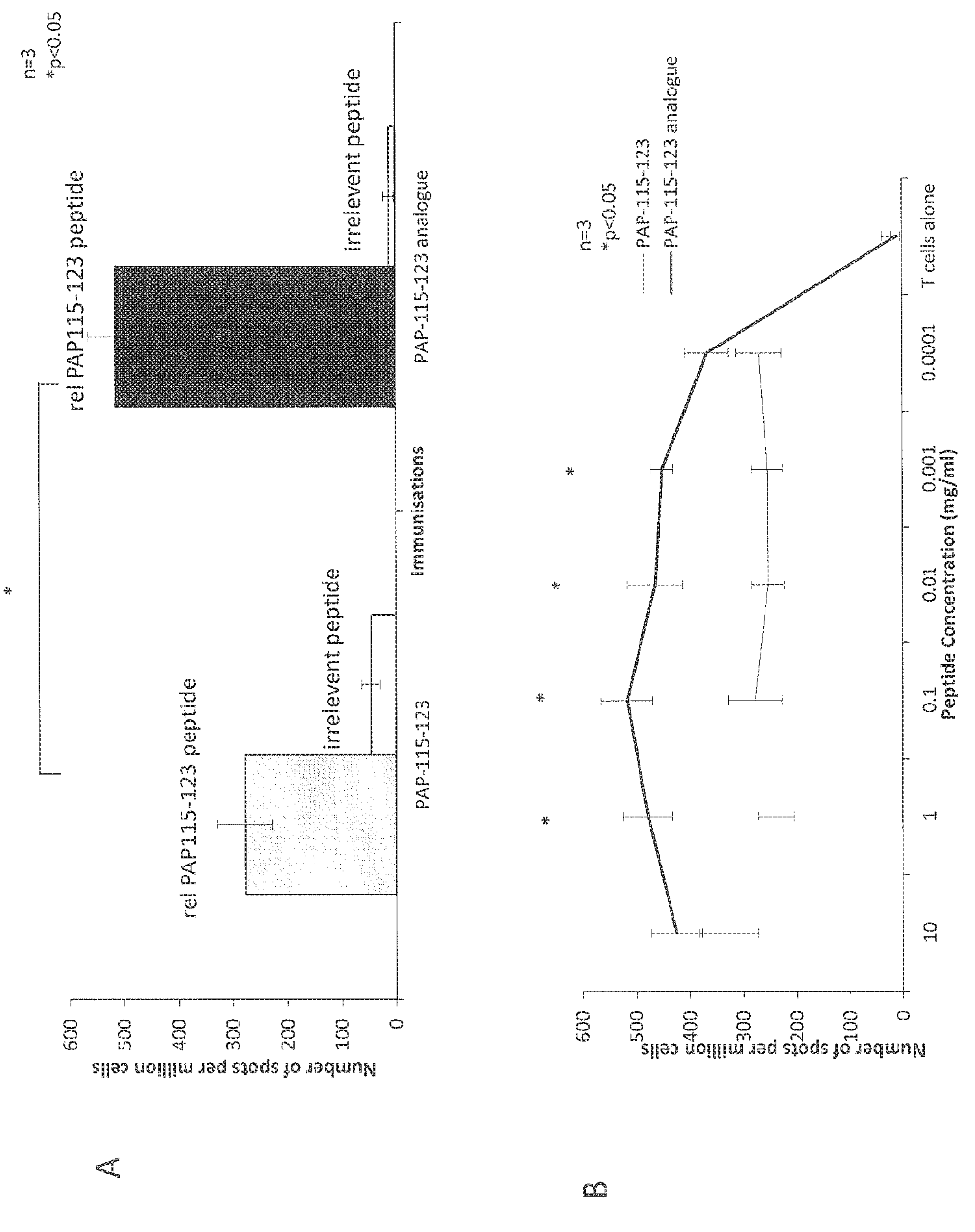
FIG. 9. Comparison of IFNγ responses induced by PAP-115-123 peptide and PAP-115-123 analogue peptide immunisation (A) and to varying PAP-115-123 peptide/analogue peptide concentrations (B), as determined using an ex vivo ELISPOT. C57Bl/6 mice in the PAP-115-123 peptide immunisation group were immunised with 100 μg of PAP-114-128 on day 1 and 75 μg of PAP-115-123 on day 14. C57Bl/6 mice in the PAP-115-123 analogue peptide immunisation group were immunised with 100 μg of PAP-114-128 analogue peptide on day 1 and 75 μg of PAP-115-123 on day 14. A week after the final immunisation, spleens were isolated for the ex vivo ELISPOT assay. For the assay, $1\times10^6$ splenocytes were co-cultured with 1 μg of PAP-115-123 peptide or PAP-115-123 analogue peptide. Splenocytes with no added peptide were used as control. Comparisons of means (±SEM) between groups (splenocytes pulsed with PAP-115-123 peptide or PAP-115-123 analogue peptide) are made with an unpaired t test. The experiment was performed with three mice per group.

The PAP-115-123 Analogue Peptide is a More Potent Inducer of Peptide-Specific Immune Responses in Syngeneic C57Bl/6 Mice and Transgenic HHDII/DRI Mice than PAP-115-123 Peptide The PAP-115-123 peptide which was obtained by altering the second amino acid of the sequence from alanine to lysine was predicted to have a higher HLA-2 binding score by the syfpeithi database. The binding score of PAP-115-123 epitope (SAMTNLAAL) (SEQ ID NO. 13) to HLA-A2.1 was 24 and that of the analogue peptide (SLMTNLAAL) (SEQ ID NO. 8) was 30. The immunogenicity of PAP-115-123 epitope and its analogue epitope was assessed by immunising syngeneic C57Bl/6 mice with these peptides. C57Bl/6 mice were immunised with 100 μg of PAP-114-128 on day 1 and 75 g of PAP-115-123 on day 14 or 100 μg of PAP-114-128 analogue peptide on day 1 and 75 g of PAP-115-123 on day 14. A week after the final immunisation spleens were isolated for the ex vivo ELISPOT assay. For this, $1\times10^6$ splenocytes were co-cultured with 1 μg of PAP-115-123 peptide or PAP-115-123 analogue peptide. Splenocytes with no added peptide were used as control. A 2-fold higher IFNγ response by splenocytes from animals immunised with the PAP-114-128 analogue peptide was observed (FIG. 9A). The number of spots in generated by splenocytes from PAP-114-128 immunised animals was 280, whereas the number of spots generated by splenocytes from PAP-114-128 analogue immunised animals was 590. Comparisons of means (±SEM) between groups (splenocytes pulsed with PAP-114-128 peptide or PAP-114-128 analogue peptide) were performed using the unpaired t test, and there were 3 animals in each group. Peptide-specific IFNγ responses generated by splenocytes that had been pulsed with varying concentrations (10, 1, 0.1, 0.01, 0.001 and 0.0001 mg/ml) of PAP-15-123 epitope or analogue epitope were also evaluated. A significantly higher IFNγ response was generated by splenocytes from animals that had been immunised with the analogue peptide at peptide concentrations of 1, 0.1, 0.01 and 0.001 mg/ml (unpaired t-test, $p<0.05$, FIG. 9B).

Figure 10:
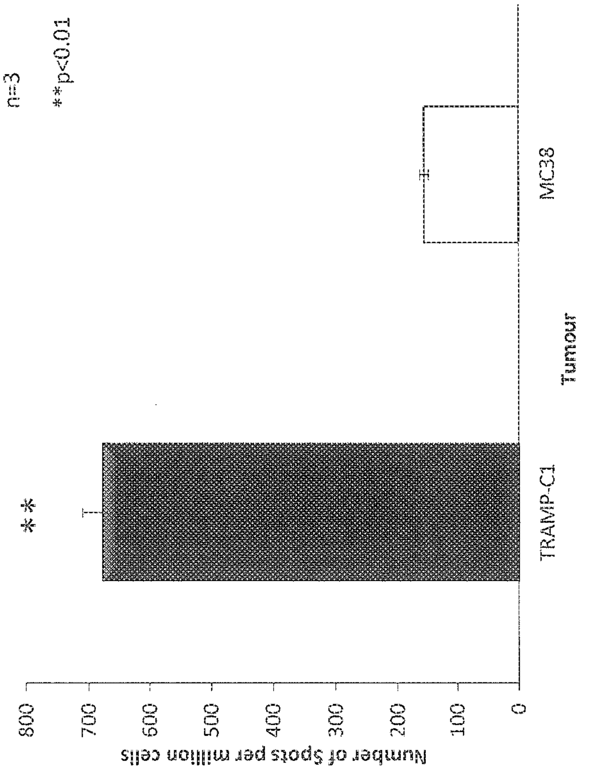
FIG. 10. Comparison of IFNγ responses generated by splenocytes from mice that have been immunised with PAP-115-123 analogue peptide, and which have been co-cultured with TRAMP-C1 cells and MC38 cells, as determined using an ex vivo ELISPOT. C57Bl/6 mice were immunised with 100 μg of PAP-114-128 analogue peptide on day 1 and 75 μg of PAP-115-123 on day 14. Splenocytes were isolated for the ex vivo ELISPOT assay a week after the final immunisation. For the assay, $1\times10^6$ splenocytes were co-cultured with $1\times10^5$ TRAMP-C1 'stimulator' cells. Control wells received $1\times10^5$ MC38 cells as stimulator cells. Comparisons of means (±SEM) between groups (splenocytes pulsed with TRAMP-C1 or MC38) are made using an unpaired t test. The experiment was performed with three mice per group.
Figure 11:
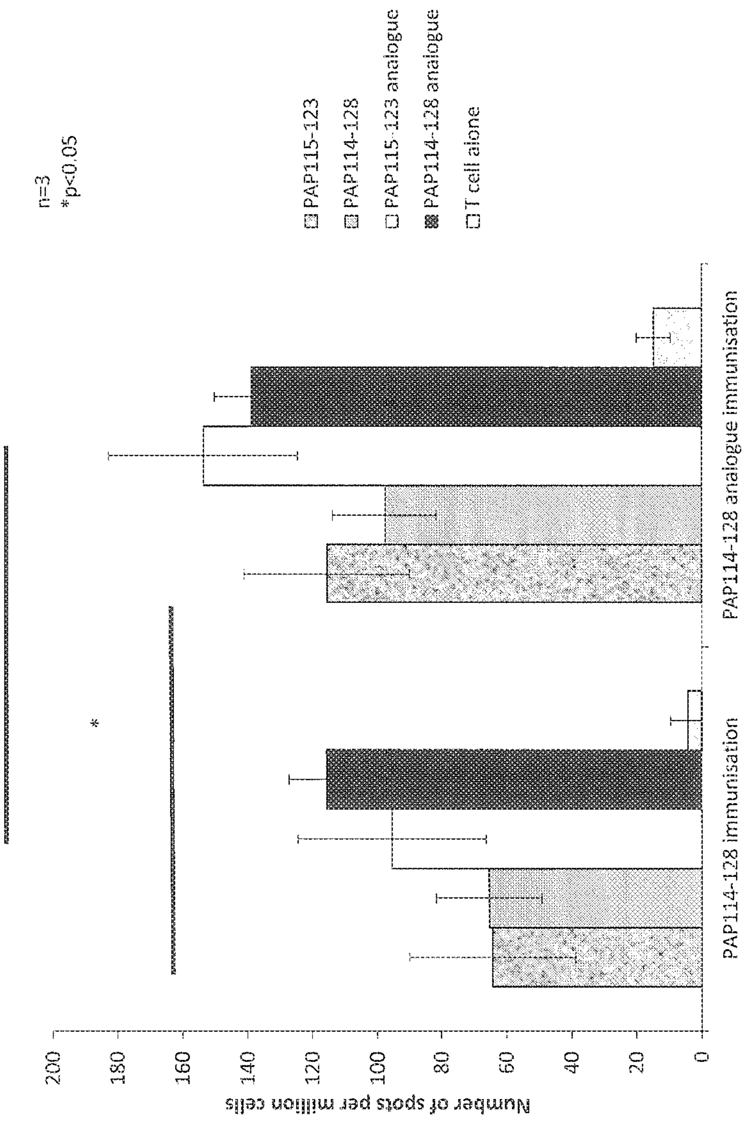
FIG. 11. Comparison of IFNγ responses generated by splenocytes isolated from HHDII/DRI mice that have been immunised with PAP-114-128 peptide and PAP-114-128 analogue peptide, as determined using an ex vivo ELISPOT. HHDII/DRI mice were immunised with 100 μg of PAP-114-128 on day 1 and 75 μg of PAP-115-123 on day 14, or 100 μg of PAP-114-128 analogue peptide on day 1 and 75 μg of PAP-115-123 on day 14. Splenocytes were isolated for the ex vivo ELISPOT assay a week after the final immunisation. For the assay, $1\times10^6$ splenocytes were co-cultured with 1 μg of class I PAP-115-123 peptide or PAP-115-123 analogue peptide or 10 μg of class II PAP-114-128 peptide or PAP-114-128 analogue peptide. Splenocytes with no added peptide were used as control. Comparisons of means (±SEM) between groups (splenocytes pulsed with class I/class II peptide or class I/class II analogue peptide) are made using an unpaired t test. The experiment was performed with three mice per group.

To assess whether the T cells generated following PAP-114-128 analogue peptide immunisation could recognise naturally processed PAP-115-123 epitopes, the IFNγ response of splenocytes from the immunised mice that had been co-cultured with TRAMP-C1 cells (that naturally express PAP) was assessed using the ELISPOT. For this, $1\times10^6$ splenocytes were co-cultured with $1\times10^5$ TRAMP-C1 cells as stimulator cells. Control wells received $1\times10^5$ MC38 (that do not express PAP) cells as stimulators. Significantly higher IFNγ responses were seen using splenocytes that had been isolated from mice that had been immunised with the PAP-114-128 analogue peptide and co-cultured with TRAMP-C1 cells (unpaired t-test, $p<0.05$) (FIG. 10). The number of spots generated by co-culture splenocytes with TRAMP-C1 cells was 650, whereas and number of spots obtained when using MC38 cells as stimulators was 100. The experiment was performed with three mice per group.

The immunogenic efficiencies of the PAP-115-123 epitope peptide and the PAP-115-123 analogue peptides were further compared using transgenic HHDII/DRI mice. For this, HHDII/DRI mice in the PAP-114-128 peptide immunisation group were immunised with 100 μg of PAP-114-128 on day 1 and 75 μg of PAP-115-123 on day 14. HHDII/DRI mice in the PAP-114-128 analogue peptide immunisation group was immunised with 100 μg of PAP-114-128 analogue peptide on day 1 and 75 μg of PAP-115-123 on day 14. A week after the final immunisation spleens were isolated for the ex vivo ELISPOT assay. For the assay, $1\times10^6$ splenocytes were co-cultured with 1 μg of class I PAP-115-123 peptide or PAP-115-123 analogue peptide or 10 μg of class II PAP-114-128 peptide or PAP-114-128 analogue peptide. Splenocytes with no added peptide were used as control. Splenocytes isolated from PAP-115-123 analogue peptide immunised group generated a significantly higher IFNγ response when co-cultured with class I PAP115-123 and PAP-115-123 analogue peptide epitopes (unpaired t-test, $p<0.05$) (FIG. 5.9). No significant IFNγ response was seen when splenocytes were co-cultured with PAP-114-128 class II epitope. The experiment was performed with three mice per group.

PAP-115-123 Specific IFNγ Responses in PBMCs from Patients with Prostate Cancer

Figure 2:
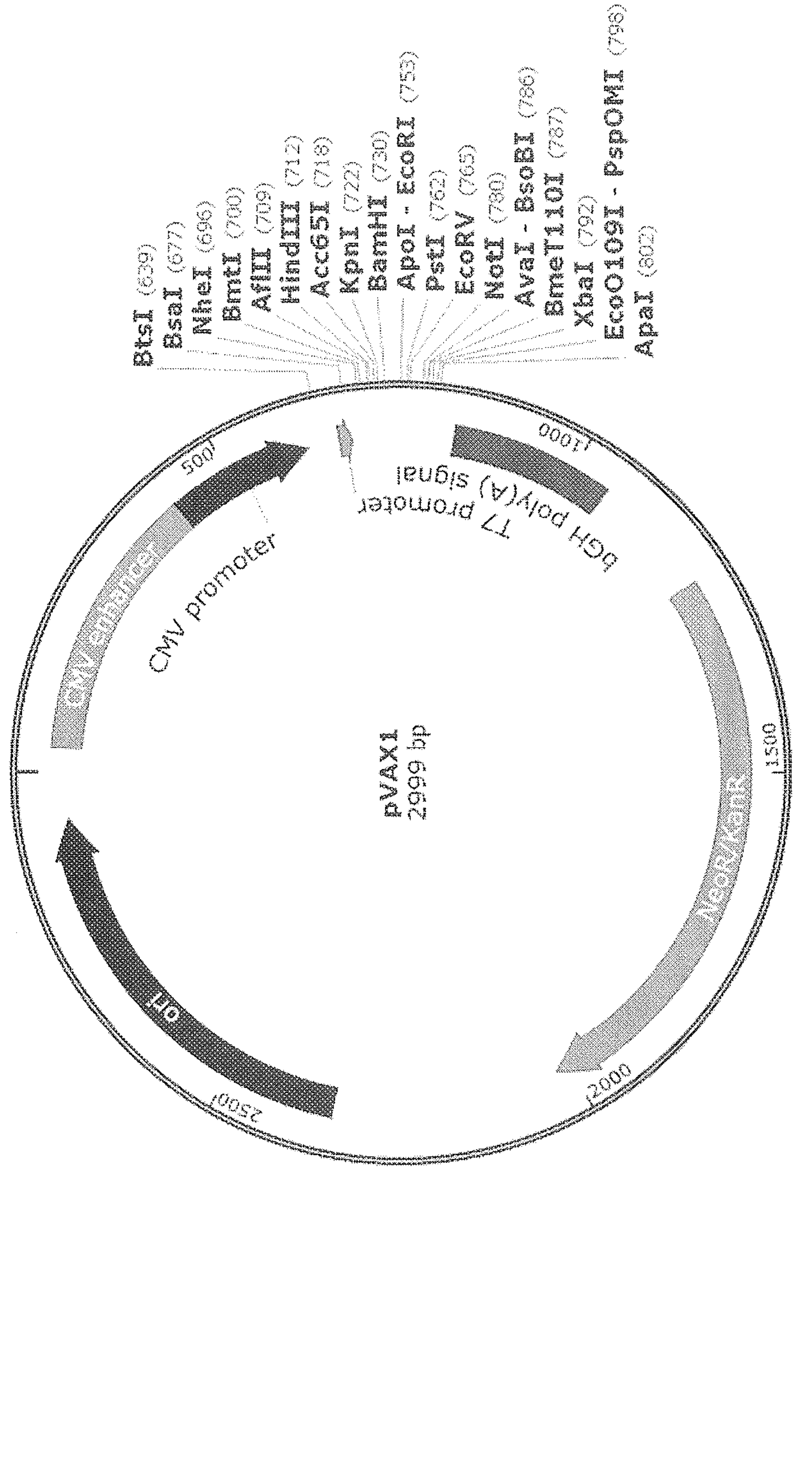
FIG. 2 shows a schematic diagram of the pVAX1™ vector.
Figure 3:
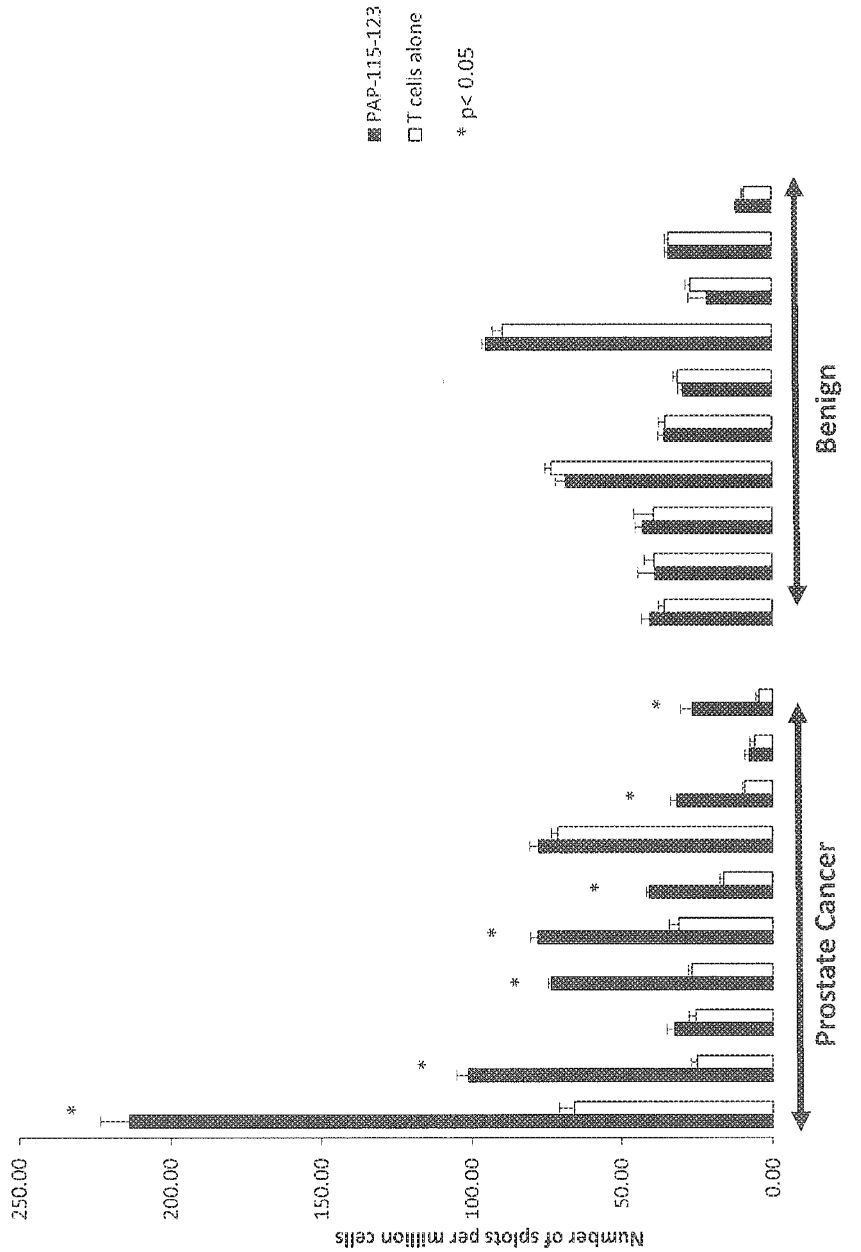
FIG. 3. IFNγ response of peripheral blood mononuclear cells (PBMCs) isolated from patients with prostate cancer and individuals with benign disease after re-stimulation with PAP-115-123 epitope using an ELISPOT assay. Cryopreserved PBMCs from ten HLA-A2 positive prostate cancer patients and ten benign candidates were compared. The PBMCs were cultured in vitro with 5 μg of PAP-114-128 epitope for 7 days. The cells were then washed and rested overnight and $4\times10^4$ cells were added to each well of an ELISPOT plate. PAP-115-123 epitope peptide (1 μg) was added per well and cells cultured for 48 hours. The plates were then washed according to the manufacturer's protocol. PBMCs with no added peptide were used as control. Comparisons of means (±SEM) between groups (cells pulsed with PAP-115-123 or no peptide) are made using an unpaired t test.
Figure 12:
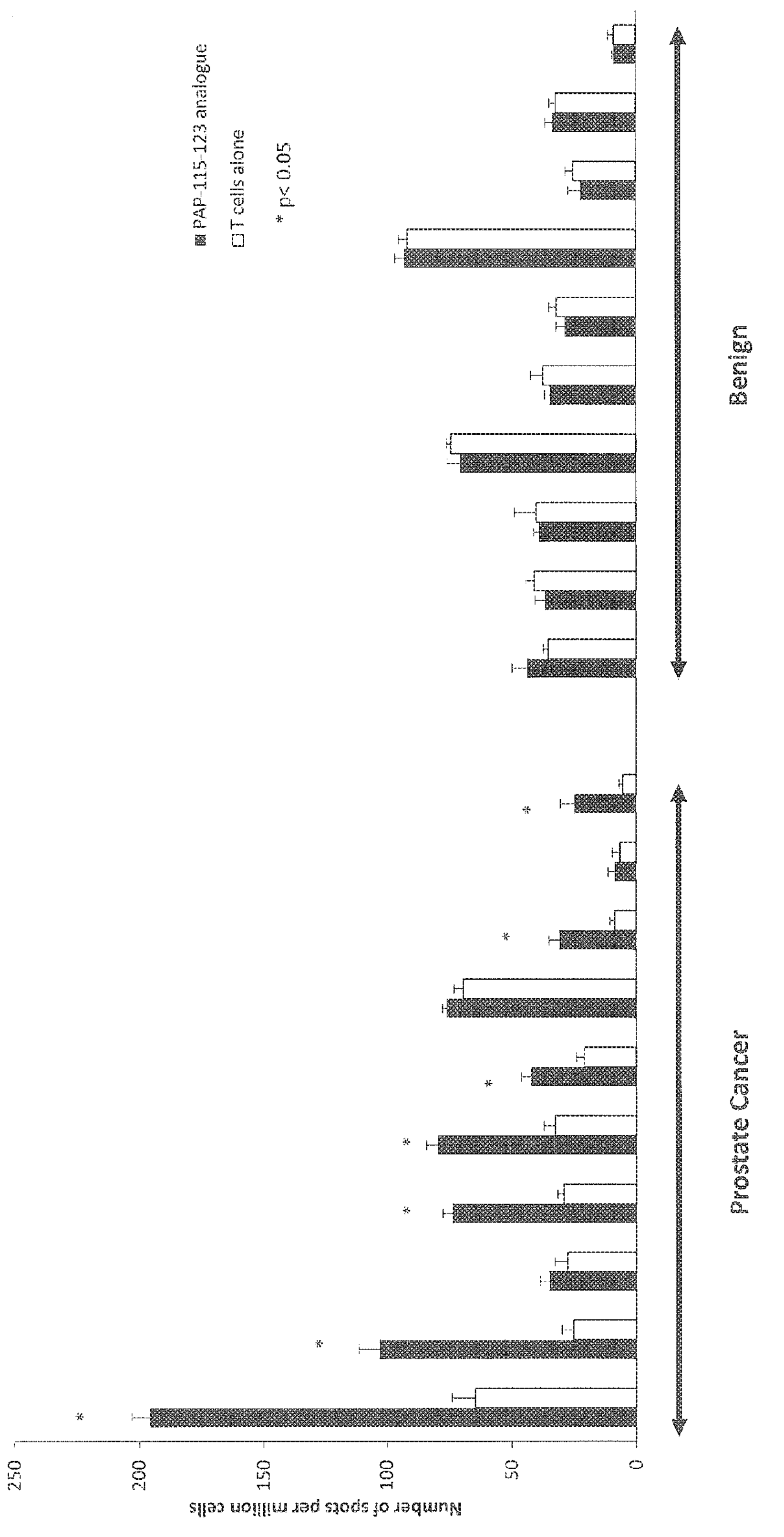
FIG. 12. IFNγ responses generated by PBMCs isolated from 10 patients with prostate cancer and 10 individuals with benign disease after re-stimulation with the PAP-115-123 analogue epitope peptide, as determined using an ELISPOT assay. PBMCs were cultured in vitro with 5 μg of PAP-114-128 analogue epitope for 7 days. The cells were then washed and rested overnight, at which time and $4\times10^4$ cells were added to each well of an ELISPOT plate. PAP-115-123 analogue epitope peptide (1 μg) was added to each well and the cells were cultured for 48 hours. The plates were then washed according to the manufacturer's protocol. PBMCs cultured with no added peptide were used as the control. Comparisons of means (±SEM) between groups (PBMCs pulsed with PAP-115-123 analogue or no peptide) are made using an unpaired t test.

To determine the presence of circulating T cells specific for PAP-115-123 analogue peptide in humans, PBMCs from HLA-A2 positive patients with prostate cancer and individuals with benign disease were used. Cryopreserved PBMCs were thawed, washed and restimulated for 7 days with PAP-114-129 analogue epitope. The cells were then washed and rested overnight, at which time $4\times10^4$ cells were added to each well of an ELISPOT plate. 1 μg of PAP-115-123 analogue epitope was added to each well and cells were cultured for 48 hours. The plates were developed as per the manufacturer's instructions. PBMCs cultured with no peptide were used as control. A PAP-115-123 analogue specific IFNγ response was seen in 7 of the 10 PBMC samples from patients with prostate cancer, and this was significantly higher than the response which was observed in controls control (splenocytes pulsed with no peptide) (unpaired t-test, $p<0.05$) (FIG. 12). The number of IFNγ spots in one of the patients was as high as 180 spots compared to control (54 spots). Similar response was also obtained when PBMCs were co-cultured with PAP-115-123 epitope (FIG. 3). The number of spots generated by PBMCs from the 6 patients with prostate cancer patients ranged between 50 and 100 (vs 10-20 in control wells). Although some of the samples from individuals with benign disease generated 50-100 spots, the number of spots in the control wells was also high. Hence, no PAP-115-123 analogue specific IFNγ response was seen in any of the PBMC samples from individuals with benign disease.

Discussion

PAP has emerged as a widely studied target antigen against prostate cancer in particular after clinical trials showing clinical benefits in patients treated with vaccines targeting PAP by different modes of antigen presentation (Higano et al., 2009, Johnson et al., 2006). An immunogenic class II PAP epitope PAP-114-128 that incorporates class I PAP-115-123 has been identified and pre-existing T cells that are specific for these epitopes have been identified in HLA-A2 positive patients with prostate cancer.

Although benign growth of the prostate gland is accompanied by a significant increase in the proliferation rate of epithelial cells, these do not frequently progress to malignancy (Cole et al., 1999). Hence, comparing the responsiveness of PBMCs from patients with malignant disease and individuals with benign disease is likely to provide vital information relating to malignant transformation in prostate cancer. Significant PAP-115-123 specific IFNγ responses have been seen in PBMCs from 7 out of the 10 patients with prostate cancer that have been tested. Interestingly, none of the PBMC samples from individuals with benign disease exhibited a PAP peptide-specific IFNγ response.

PAP-115-123 specific IFNγ responses by PBMCs from patients with prostate cancer that have participated in a phase I/II clinical study of a vaccine which is based on the administration of autologous DCs that have been transfected with mRNA from allogeneic prostate cancer cell lines (DU145, LNCAP and PC3), all of which express PAP, has also been assessed. Out of the 8 PBMC samples tested, 6 of those that were obtained post-vaccination exhibited a significantly greater PAP-115-123 specific IFNγ response than samples that were obtained prior to vaccination. A similar response was seen when different concentrations (10 μg and 1 μg) of PAP-115-123 epitope was used to stimulate the PBMCs.

The patients in the clinical trial had been categorised as being ‘responders’ or ‘non-responders’ using a decrease and increase in the log slope of PSA as surrogate indicators for clinical response respectively. In the current study, a correlation between PAP-115-123 specific T cell response and a favourable early clinical outcome was apparent, in that a 2-4 fold increase in PAP-115-123 specific IFNγ response was seen in responders and a 2-10 fold decrease in response was found associated with the non-responders, when the pre-vaccination sample was compared to the post vaccination samples. ELISAs performed on the supernatants harvested from these cultures confirmed these findings.

It has been reported that modification of single anchor residues can improve MHC class I binding and extend the time period which is available for T cells to recognise the presented peptide (Nicola et al., 2013). Similar modifications have been reported to induce effective immune responses against a range of tumour types such as leukemias and solid tumours, and some have now shown promise in phase I clinical trials (Christensen et al., 2009, Fourcade et al., 2008). The current study has demonstrated that the binding coefficient to HLA-A2.1, as predicted by syfpeithi database increases from 25 to 33 when alanine in the second position is replaced with lysine, whereas the binding coefficient to the H2Kb of mice remains unchanged. Immunisation of C57Bl/6 mice and HHDII/DRI mice with PAP-114-128 analogue peptide induces significantly more potent immune responses, on the basis of the IFNγ response, compared to immunisation with PAP-114-128. The T cells generated in C57Bl/6 mice were able to lyse TRAMP-C1 cells that express PAP, showing that it could be naturally processed. The enhanced IFNγ response induced in splenocytes was observed over a range of PAP-115-123 peptide concentrations. Interestingly, the responsiveness of PBMCS from patients with prostate cancer to the PAP115-123 analogue peptide was also greater, and PBMCs from individuals with benign disease are not responsive These findings clearly demonstrate the potential presence of a PAP repertoire in humans. Furthermore, the ability to detect T cell responsiveness to PAP-related peptides in the circulation of patients with breast cancer could be used as a biomarker to determine the development of therapeutic immune response to a vaccination strategy. This would also allow evaluation of optimal booster immunisation schedules.

The current data continue our development and characterisation of PAP-based vaccines and provides the first modified PAP antigen immunogenic peptide for inclusion in a PAP-based vaccine.

REFERENCES

1. Boyle P, Ferlay J. Cancer incidence and mortality in Europe, 2004. Annals of Oncology 2005 March; 16[3]: 481-8.
2. Siegel R, Naishadham D, Jemal A. Cancer Statistics. CA CANCER J CLIN 2013; 63:11-30.
3. Snyder A, Tepper J E, Slovin S F. Perspectives on immunotherapy in prostate cancer and solid tumors: where is the future? Semin Oncol. 2013 June; 40[3]: 347-60
4. J Am Board Fam Pract. 2003 March-April; 16[2]:95-101.
5. O'Keefe D S, Bacich D J, Heston W D. Comparative analysis of prostate-specific membrane antigen [PSMA] versus a prostate-specific membrane antigen-like gene. Prostate. 2004 Feb. 1; 58[2]:200-10.
6. Cunha A C, Weigle B, Kiessling A, Bachmann M, Rieber E P. Tissue-specificity of prostate specific antigens: comparative analysis of transcript levels in prostate and non-prostatic tissues. Cancer Letters. 2006 May 18; 236[2]: 229-38.
7. Gupta S, Carballido E, Fishman M. Sipuleucel-T for therapy of asymptomatic or minimally symptomatic, castrate-refractory prostate cancer: an update and perspective among other treatments. OncoTargets and Therapy. 2011; 4:79-96.
8. Speetjens F M, Kuppen P J, Welters M J, Essahsah F, Voet van den Brink A M, Lantrua M G, et al. Induction of p53-specific immunity by a p53 synthetic long peptide vaccine in patients treated for metastatic colorectal cancer. Clinical Cancer Research 2009 Feb. 1; 15[3]:1086-95.
9. Durrant L G, Pudney V A, Spendlove I. Using monoclonal antibodies to stimulate antitumor cellular immunity. Expert Review of Vaccines. 2011 July; 10[7]:1093-106.
10. Christensen O, Lupu A, Schmidt S, Condomines M, Belle S, Maier A, Hose D, Neuber B, Moos M, Kleist C, Terness P, Ho A D, Gold-schmidt H, Klein B, Hundemer M. Melan-A/MART1 analog peptide triggers anti-myeloma T cells through crossreactivity with HM1.24. J Immunother 2009; (32): 613-621.
11. Cole K. A., Krizman D. B., Emmert-Burk M. R. The genetics of cancer—a 3D model. Nat. Genet 1999; (21): 38-41
12. Fourcade J, Kudela P, Andrade Filho P A, Janjic B, Land S R, Sander C, Krieg A, Donnenberg A, Shen H, Kirkwood J M, Zarour H M. Immunization with analog peptide in combination with CpG and montanide expands tumor antigen-specific $CD8^+$ T cells in melanoma patients. J Immunother 2008; (31): 781-791.
13. Higano C S, Schellhammer P F, Small E J, Burch P A, Nemunaitis J, Yuh L, Provost N, Frohlich M W Integrated data from 2 randomized, double-blind, placebo-controlled, phase 3 trials of active cellular immunotherapy with sipuleucel-T in advanced prostate cancer, Cancer 2009; (115):3670-3679

14. Johnson L E, Frye T P, Arnot A R, Marquette C, Couture L A, Gendron-Fitzpatrick A, McNeel D G Safety and immunological efficacy of a prostate cancer plasmid DNA vaccine encoding prostatic acid phosphatase (PAP) Vaccine 2006; (24):293-303

15. Nicola H, Sarah B, Wendy I, Ghazala K h, Gisella V, Jason R, Karen P, Ghulam M, Freda S and Barbara-ann G An analogue peptide from the Cancer/Testis antigen PASD1 induces CD8+ T cell responses against naturally processed peptide Cancer Immunity 2013; (1):16

The invention claimed is:

1. A composition comprising a polypeptide of 9-42 amino acids, the polypeptide comprising at least amino acids 13-21 of SEQ ID No: 1 and said amino acids 13-21 of SEQ ID No: 1 has HLA-A2 haplotype binding activity.

2. A composition according to claim 1, wherein the polypeptide comprises amino acids 12-26 of SEQ ID No: 1.

3. A composition according to claim 1, wherein the polypeptide comprises amino acids 8-22 of SEQ ID No: 1.

4. A composition according to claim 1, wherein the polypeptide comprises amino acids 13-42 of SEQ ID No: 1.

5. A composition according to claim 1, wherein the polypeptide comprises amino acids 9-23 of SEQ ID No: 1.

6. A composition according to claim 1, wherein the polypeptide comprises amino acids 1-42 of SEQ ID No: 1.

7. A composition according to claim 1, wherein the polypeptide consists essentially of amino acids 13-21, 12-26, 1-42 or 8-22 of SEQ ID No: 1.

8. A composition comprising a polynucleotide sequence, wherein the polynucleotide sequence comprises at least a first polynucleotide sequence encoding a first polypeptide of 9-42 amino acids, wherein the first polypeptide comprises at least amino acids 13-21 of SEQ ID No: 1 and said amino acids 13-21 of SEQ ID No: 1 has HLA-A2 haplotype binding activity.

9. A composition according to claim 8, wherein the polynucleotide sequence further comprises a second polynucleotide sequence, the second polynucleotide sequence encoding an immunoglobulin or a fragment of an immunoglobulin.

10. A composition according to claim 8, wherein the polynucleotide sequence further comprises a second polynucleotide sequence, the second polynucleotide sequence encoding a second polypeptide, the second polypeptide encoding at least one of HSP-70, Shiga toxin and GM-CSF, CpG, PolyIC or alpha-Gal-Cer, wherein upon translation, the first and second polypeptides comprise a fusion protein.

11. A composition according to claim 8, wherein the polynucleotide sequence further comprises a second polynucleotide sequence, the second polynucleotide sequence encoding a second polypeptide, the second polypeptide encoding at least one of a ubiquitin or a secretory leader sequence, wherein upon translation, the first and second polypeptides comprise a fusion protein.

12. A composition according to claim 8, wherein the polynucleotide sequence is incorporated into a pVAX1 or GVAX vector.

13. A composition according to claim 8, wherein the first polypeptide comprises amino acids 12-26 of SEQ ID No 1.

14. A composition according to claim 8, wherein the first polypeptide comprises amino acids 8-22 of SEQ ID No 1.

15. A composition according to claim 8, wherein the first polypeptide comprises amino acids 13-42 of SEQ ID No 1.

16. A composition according to claim 8, wherein the first polypeptide comprises amino acids 9-23 of SEQ ID No 1.

17. A composition according to claim 8, wherein the first polypeptide comprises amino acids 1-42 of SEQ ID No 1.

18. A vaccine comprising the composition of claim 8.

19. A vaccine comprising a pharmaceutically acceptable carrier and a polypeptide of 9-42 amino acids, wherein the polypeptide comprises at least amino acids 13-21 of SEQ ID No: 1.

20. A vaccine according to claim 19, wherein the polypeptide is present in an amount effective to elicit protective antibodies against prostate cancer in an animal immunized with said vaccine.

21. A vaccine according to claim 19, wherein the polypeptide consists essentially of amino acids 13-21, 12-26, 1-42 or 8-22 of SEQ ID No: 1.

22. A vaccine comprising the composition according to claim 12.

* * * * *

SEQUENCE LISTING

```
<160> NUMBER OF SEQ ID NOS: 14

<210> SEQ ID NO 1
<211> LENGTH: 42
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with Ala to Leu change at position 115

<400> SEQUENCE: 1

Tyr Ile Arg Ser Thr Asp Val Asp Arg Thr Leu Met Ser Leu Met Thr
1               5                   10                  15

Asn Leu Ala Ala Leu Phe Pro Pro Glu Gly Val Ser Ile Trp Asn Pro
            20                  25                  30

Ile Leu Leu Trp Gln Pro Ile Pro Val His
        35                  40


<210> SEQ ID NO 2
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding
      position 14 of peptide

<400> SEQUENCE: 2

tatattcgaa gcacagacgt tgaccggact ttgatgagtc ttatgacaaa cctggcagcc      60

ctgtttcccc cagaaggtgt cagcatctgg aatcctatcc tactctggca gcccatcccg     120

gtgcac                                                                126


<210> SEQ ID NO 3
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding
      position 14 of peptide

<400> SEQUENCE: 3

tatattcgaa gcacagacgt tgaccggact ttgatgagtc tcatgacaaa cctggcagcc      60

ctgtttcccc cagaaggtgt cagcatctgg aatcctatcc tactctggca gcccatcccg     120

gtgcac                                                                126


<210> SEQ ID NO 4
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding
      position 14 of peptide
```

<400> SEQUENCE: 4
tatattcgaa gcacagacgt tgaccggact ttgatgagtc taatgacaaa cctggcagcc 60
ctgtttcccc cagaaggtgt cagcatctgg aatcctatcc tactctggca gcccatcccg 120
gtgcac 126

<210> SEQ ID NO 5
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding position 14 of peptide

<400> SEQUENCE: 5
tatattcgaa gcacagacgt tgaccggact ttgatgagtc tgatgacaaa cctggcagcc 60
ctgtttcccc cagaaggtgt cagcatctgg aatcctatcc tactctggca gcccatcccg 120
gtgcac 126

<210> SEQ ID NO 6
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding position 14 of peptide

<400> SEQUENCE: 6
tatattcgaa gcacagacgt tgaccggact ttgatgagtt taatgacaaa cctggcagcc 60
ctgtttcccc cagaaggtgt cagcatctgg aatcctatcc tactctggca gcccatcccg 120
gtgcac 126

<210> SEQ ID NO 7
<211> LENGTH: 126
<212> TYPE: DNA
<213> ORGANISM: Artificial Sequence
<220> FEATURE:
<223> OTHER INFORMATION: Synthesized
<220> FEATURE:
<223> OTHER INFORMATION: PAP with A-L mutation at codon encoding position 14 of peptide

<400> SEQUENCE: 7
tatattcgaa gcacagacgt tgaccggact ttgatgagtt tgatgacaaa cctggcagcc 60
ctgtttcccc cagaaggtgt cagcatctgg aatcctatcc tactctggca gcccatcccg 120
gtgcac 126

<210> SEQ ID NO 8
<211> LENGTH: 9
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with A-L mutation at position 2 of peptide

<400> SEQUENCE: 8

Ser Leu Met Thr Asn Leu Ala Ala Leu
1               5

<210> SEQ ID NO 9
<211> LENGTH: 15
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with A-L mutation at position 3 of peptide

<400> SEQUENCE: 9

```
Met Ser Leu Met Thr Asn Leu Ala Ala Leu Phe Pro Pro Glu Gly
1               5                   10                  15
```

<210> SEQ ID NO 10
<211> LENGTH: 15
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with A-L mutation at position 7 of peptide

<400> SEQUENCE: 10

```
Asp Arg Thr Leu Met Ser Leu Met Thr Asn Leu Ala Ala Leu Phe
1               5                   10                  15
```

<210> SEQ ID NO 11
<211> LENGTH: 30
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with A-L mutation at position 2 of peptide

<400> SEQUENCE: 11

```
Ser Leu Met Thr Asn Leu Ala Ala Leu Phe Pro Pro Glu Gly Val Ser
1               5                   10                  15

Ile Trp Asn Pro Ile Leu Leu Trp Gln Pro Ile Pro Val His
            20                  25                  30
```

<210> SEQ ID NO 12
<211> LENGTH: 2999
<212> TYPE: DNA
<213> ORGANISM: Artificial Sequence
<220> FEATURE:
<223> OTHER INFORMATION: Synthesized
<220> FEATURE:
<223> OTHER INFORMATION: pVAX1 vector sequence

<400> SEQUENCE: 12

```
gactcttcgc gatgtacggg ccagatatac gcgttgacat tgattattga ctagttatta      60

atagtaatca attacggggt cattagttca tagcccatat atggagttcc gcgttacata     120

acttacggta aatggcccgc ctggctgacc gcccaacgac ccccgcccat tgacgtcaat     180

aatgacgtat gttcccatag taacgccaat agggactttc cattgacgtc aatgggtgga     240

ctatttacgg taaactgccc acttggcagt acatcaagtg tatcatatgc caagtacgcc     300

ccctattgac gtcaatgacg gtaaatggcc cgcctggcat tatgcccagt acatgacctt     360

atgggacttt cctacttggc agtacatcta cgtattagtc atcgctatta ccatggtgat     420

gcggttttgg cagtacatca atgggcgtgg atagcggttt gactcacggg gatttccaag     480

tctccacccc attgacgtca atgggagttt gttttggcac caaaatcaac gggactttcc     540
```

-continued

```
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccactag tccagtgtgg tggaattctg cagatatcca gcacagtggc    780
ggccgctcga gtctagaggg cccgtttaaa cccgctgatc agcctcgact gtgccttcta    840
gttgccagcc atctgttgtt tgcccctccc ccgtgccttc cttgaccctg gaaggtgcca    900
ctcccactgt cctttcctaa taaaatgagg aaattgcatc gcattgtctg agtaggtgtc    960
attctattct ggggggtggg gtggggcagg acagcaaggg ggaggattgg gaagacaata   1020
gcaggcatgc tggggatgcg gtgggctcta tggcttctac tgggcggttt tatggacagc   1080
aagcgaaccg gaattgccag ctggggcgcc ctctggtaag gttgggaagc cctgcaaagt   1140
aaactggatg gctttctcgc cgccaaggat ctgatggcgc aggggatcaa gctctgatca   1200
agagacagga tgaggatcgt ttcgcatgat tgaacaagat ggattgcacg caggttctcc   1260
ggccgcttgg gtggagaggc tattcggcta tgactgggca caacagacaa tcggctgctc   1320
tgatgccgcc gtgttccggc tgtcagcgca ggggcgcccg gttctttttg tcaagaccga   1380
cctgtccggt gccctgaatg aactgcaaga cgaggcagcg cggctatcgt ggctggccac   1440
gacgggcgtt ccttgcgcag ctgtgctcga cgttgtcact gaagcgggaa gggactggct   1500
gctattgggc gaagtgccgg ggcaggatct cctgtcatct caccttgctc ctgccgagaa   1560
agtatccatc atggctgatg caatgcggcg gctgcatacg cttgatccgg ctacctgccc   1620
attcgaccac caagcgaaac atcgcatcga gcgagcacgt actcggatgg aagccggtct   1680
tgtcgatcag gatgatctgg acgaagagca tcaggggctc gcgccagccg aactgttcgc   1740
caggctcaag gcgagcatgc ccgacggcga ggatctcgtc gtgacccatg gcgatgcctg   1800
cttgccgaat atcatggtgg aaaatggccg cttttctgga ttcatcgact gtggccggct   1860
gggtgtggcg gaccgctatc aggacatagc gttggctacc cgtgatattg ctgaagagct   1920
tggcggcgaa tgggctgacc gcttcctcgt gctttacggt atcgccgctc ccgattcgca   1980
gcgcatcgcc ttctatcgcc ttcttgacga gttcttctga attattaacg cttacaattt   2040
cctgatgcgg tattttctcc ttacgcatct gtgcggtatt tcacaccgca tacaggtggc   2100
acttttcggg gaaatgtgcg cggaacccct atttgtttat ttttctaaat acattcaaat   2160
atgtatccgc tcatgagaca ataaccctga taaatgcttc aataatagca cgtgctaaaa   2220
cttcattttt aatttaaaag gatctaggtg aagatccttt ttgataatct catgaccaaa   2280
atcccttaac gtgagttttc gttccactga gcgtcagacc ccgtagaaaa gatcaaagga   2340
tcttcttgag atcctttttt tctgcgcgta atctgctgct tgcaaacaaa aaaaccaccg   2400
ctaccagcgg tggtttgttt gccggatcaa gagctaccaa ctctttttcc gaaggtaact   2460
ggcttcagca gagcgcagat accaaatact gtccttctag tgtagccgta gttaggccac   2520
cacttcaaga actctgtagc accgcctaca tacctcgctc tgctaatcct gttaccagtg   2580
gctgctgcca gtggcgataa gtcgtgtctt accgggttgg actcaagacg atagttaccg   2640
gataaggcgc agcggtcggg ctgaacgggg ggttcgtgca cacagcccag cttggagcga   2700
acgacctaca ccgaactgag atacctacag cgtgagctat gagaaagcgc cacgcttccc   2760
gaagggagaa aggcggacag gtatccggta agcggcaggg tcggaacagg agagcgcacg   2820
agggagcttc caggggggaaa cgcctggtat ctttatagtc ctgtcgggtt tcgccacctc   2880
tgacttgagc gtcgattttt gtgatgctcg tcaggggggc ggagcctatg gaaaaacgcc   2940
```

-continued

```
agcaacgcgg cctttttacg gttcctgggc ttttgctggc cttttgctca catgttctt    2999


<210> SEQ ID NO 13
<211> LENGTH: 9
<212> TYPE: PRT
<213> ORGANISM: Homo sapiens

<400> SEQUENCE: 13

Ser Ala Met Thr Asn Leu Ala Ala Leu
1               5


<210> SEQ ID NO 14
<211> LENGTH: 15
<212> TYPE: PRT
<213> ORGANISM: Artificial Sequence
<220> FEATURE:
<223> OTHER INFORMATION: Synthesized
<220> FEATURE:
<223> OTHER INFORMATION: PAP with mutation Ala to Leu at position 6 of
      peptide

<400> SEQUENCE: 14

Arg Thr Leu Met Ser Leu Met Thr Asn Leu Ala Ala Leu Phe Pro
1               5                   10                  15
```